(12) United States Patent
Zare et al.

(10) Patent No.: US 10,370,671 B2
(45) Date of Patent: Aug. 6, 2019

(54) BINARY VECTORS WITH MINIMIZED BIOSAFETY CONCERNS AND HIGH TRANSFORMATION RATES BY ENGINEERED PLANT-DERIVED TRANSFER-DNA

(71) Applicants: Bahar Zare, Karaj (IR); Mohammad Ali Malboobi, Tehran (IR); Mohammad Sadegh Sabet Jahromi, Fars Province (IR); Peyman Norouzi, Karaj (IR)

(72) Inventors: Bahar Zare, Karaj (IR); Mohammad Ali Malboobi, Tehran (IR); Mohammad Sadegh Sabet Jahromi, Fars Province (IR); Peyman Norouzi, Karaj (IR)

( * ) Notice: Subject to any disclaimer, the term of this patent is extended or adjusted under 35 U.S.C. 154(b) by 183 days.

(21) Appl. No.: 15/299,380

(22) Filed: Oct. 20, 2016

(65) Prior Publication Data

US 2017/0260537 A1    Sep. 14, 2017

(51) Int. Cl.
*C12N 15/82* (2006.01)

(52) U.S. Cl.
CPC ......... *C12N 15/8216* (2013.01); *C12N 15/82* (2013.01)

(58) Field of Classification Search
None
See application file for complete search history.

(56) References Cited

U.S. PATENT DOCUMENTS

| | | |
|---|---|---|
| 5,733,744 A | 3/1998 | Hamilton |
| 5,997,439 A | 12/1999 | Ohsuga et al. |
| 7,138,267 B1 | 11/2006 | Jendrisak et al. |
| 7,611,898 B2 | 11/2009 | Wang et al. |

FOREIGN PATENT DOCUMENTS

| | | |
|---|---|---|
| EP | 3066915 A1 | 9/2016 |
| WO | 2002040641 A2 | 5/2002 |

OTHER PUBLICATIONS

GenBank: FR852871.1.*
Gen Bank: FR852867.1.*
Johzuka-Hisatomi et al (Efficient transfer of base changes from a vector to the rice genome by homologous recombination: involvement of heteroduplex formation and mismatch correction. Nucleic Acids Research, vol. 36, 4727-4735, 2008).*

\* cited by examiner

*Primary Examiner* — Medina A Ibrahim
*Assistant Examiner* — Wayne Zhong
(74) *Attorney, Agent, or Firm* — NovoTechIP International PLLC

(57) ABSTRACT

An engineered plant-derived transfer (P-)DNA was designed and constructed based on a couple of T-DNA homologous sequences in sugar beet genome. Plant transformation efficacy of the engineered P-DNA was analyzed compared to conventional T-DNA in two independent systems, stable transformation of tobacco plant and sugar beet hairy roots. The outcomes demonstrated that plant transformation is directed well by vectors carrying the engineered P-DNA with higher efficiency than the conventional binary vector in both experimental systems. This vector was further improved by adding two matrix attachment regions within P-DNA. This new vector was even more efficient in gene transfer, higher than conventional binary vector.

10 Claims, 6 Drawing Sheets
(5 of 6 Drawing Sheet(s) Filed in Color)
Specification includes a Sequence Listing.

ACR region {
GTCGACCCGAGGGGAACCCTGTGGTTGGCATGCACATACAAATGGACGAACGGATA
AACCTTTTCACGCCCTTTTAAATATCCGATTATTCTAATAAACGCTCTTTTCTCTTAG
}

GTTTACTATGGAATATATCCTGGGTGTGGCCGAAGTCTGTTCGGGAAGCTTTAATTC
        RB                                    DR

AATGGGTTTACCCAAAGAAAGGAAAATTCTTCAAACAAATTTGAGCTCTGCATCTTT

TCAAGGTACCATTATATGGTCAGTGTGCTCGAGAGAGAGAAATGAATCTAGAATTTT

CAAGCGGCCGCAACAAATATCGATTCGCCTCTGGAAAAGGGAGGACGTGCTATATT

GATTTTTGATTCACTCTCAAGCTTGCCCTTATATTACATGTCGATATATCCTGCCCAA
  UL                                             LB
GCTTCCAGCCAGCCAACAGCTCCCCGACCAGATCTGTCGAC    (SEQ ID NO: 1)   } C-clusters

FIG. 1

BINARY VECTORS WITH MINIMIZED BIOSAFETY CONCERNS AND HIGH TRANSFORMATION RATES BY ENGINEERED PLANT-DERIVED TRANSFER-DNA

CROSS REFERENCE TO RELATED APPLICATION

This application claims the benefit of priority to an Iran Application Serial Number 139450140003008184 filed on Oct. 20, 2015, which is incorporated by reference herein in its entirety.

TECHNICAL FIELD

The present disclosure relates generally to the production of binary vectors with high transformation rates of any organism and more specifically plant species, that carry an engineered P-DNA sequence derived from sugar beet genome.

BACKGROUND

New transgenic crops with improved farming, food and feeding traits are progressively being developed. Although the commercialization of transgenic plants started early 1990s, necessity for analysis of unintended effects of the transgenes hampers preparing required documents for their release. Currently, *Agrobacterium*-mediated plant genetic engineering methods relies on the integration of foreign (often prokaryotic) DNA, such as transgenes, promoters, terminators and T-DNA, into plant genomes. For example, cry3 gene (GenBank Accession AY572010.1), coding for a BT protein, contains 2.7% of CpG motif, a known characteristic of prokaryotic DNA). Some interactions between inserted prokaryotic DNA and plant immune system are documented.

SUMMARY

The present application discloses a series of novel binary vectors carrying an engineered sequence that include P-DNA left and right borders (LB and RB) derived from two loci in sugar beet genome. The vectors are further comprised of modified RB flanking sequences including an upstream AC-rich region (ACR) and downstream of right border (DR), upstream of left border (UL), LB downstream sequences including a series of C-clusters and two copies of Rb7 matrix attachment regions (MAR). The effectiveness of such vectors was verified by two transformation systems, transgenic tobacco plants and sugar beet hairy roots. The transformation efficiency of the vectors was compared with a similar binary vector carrying *Agrobacterium* T-DNA, pART27.

To examine P-DNA functionality, it was substituted for conventional T-DNA in SalI restriction sites of pART27 binary vector which is a derivative of pTiC58 carrying elements such as RB, LB, ACR and C-clusters. An expression cassette carrying Pnos-nptII-Tnos encoding neomycin phosphotransferase (nptII) was also cloned between the borders of P-DNA in the ClaI restriction site of pAPB to produce pAPn vector (FIG. 3). In a sugar beet hairy root system, transformation efficiencies of the vectors were compared with a similar binary vector carrying *Agrobacterium* T-DNA, pART27. Transformation rate was defined as the PCR-positive percentage of hairy roots per leaf explants. P-DNA ability to integration of transgene into the plant cell genome was determined in comparison with conventional T-DNA. Independent transgenic tobacco plants carrying either P-DNA in pAPn or T-DNA in pART27 containing nptII expression cassette were examined. Here, transformation rate was defined as the PCR-positive percentage of regenerated plants per leaf explants. Transformation rate was increased to as high as four fold by the use of the new binary vectors.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Features of the subject technology are set forth in the appended claims. However, for purpose of explanation, several implementations of the subject technology are set forth in the following figures FIG. 1 illustrates the map of the synthesized plant-derived DNA, according to one implementation of the instant application (SEQ ID NO: 1).

DETAILED DESCRIPTION

Figure 2:
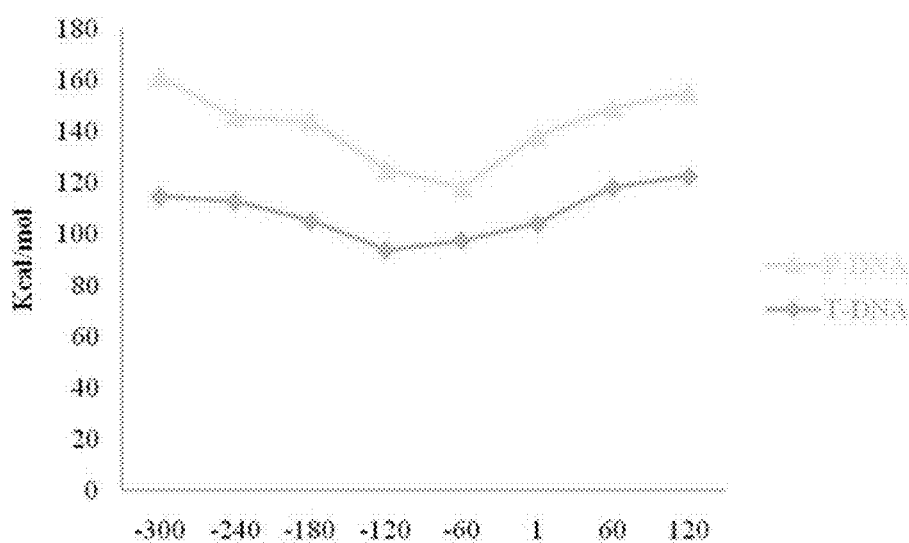
FIG. 2 illustrates the comparison between the free energy of P-DNA and T-DNA

In the following detailed description, various examples are presented to provide a thorough understanding of inventive concepts, and various aspects thereof that are set forth by this disclosure. However, upon reading the present disclosure, it may become apparent to persons of skill that various inventive concepts and aspects thereof may be practiced without one or more details shown in the examples. In other instances, well known procedures, operations and materials have been described at a relatively high-level, without detail, to avoid unnecessarily obscuring description of inventive concepts and aspects thereof.

Considering high cost of transformation and then risk assessment experiments for transgenic plants, needed for their release and commercialization, it is necessary to take possible means to increase transformation rate and to reduce required steps for risks analysis. Using P-DNA instead of conventional T-DNA in binary vectors for *Agrobacterium*-mediated plant transformation is a key feature of minimizing the presence of prokaryotic DNA in transgenic plants. In this application, a new engineered P-DNA derived from sugar beet genome was designed and successfully used for transformation of plants in two independent systems including stable transformation of tobacco and hairy roots of sugar beet. Such P-DNA fragments derived from petunia, potato, *Arabidopsis thaliana* and *Medica gotruncatula* have already been recognized by bioinformatics analysis. The potato P-DNA was used for stable plant transformation. However, the novel engineered P-DNA elements with modified UL and DR sequences and MAR sequences in the context of binary vector presented in this application is advantageous for increasing the transformation rate as well as stability of transgene expression. Plant transformation efficacy of sugar beet derived P-DNA was compared with that of conventional T-DNA. Results showed transformation efficiency of P-DNA was 2.3 and 2.2 fold higher than that of a conventional T-DNA binary vector in tobacco plants and sugar beet hairy root systems, respectively. Transformation was further increased twice by the use of MAR sequences in the context of P-DNA.

FIG. 1 shows the sequence of the engineered P-DNA derived from two loci in sugar beet genome (SEQ ID NO. 1). A 283-bp region from RB to LB (Green boxes) consists of a 208-bp sequence of RB-like (GenBank: FR852871.1) and a 75-bp sequence of LB-like (GenBank: FR852867.1) parts of sugar beet genome. A little pink box indicated the first base of LB-like part. Some elements like DR and UL were indicated by yellow boxes. ACR region and C-clusters of *Agrobacterium* pTiC58 were shown by little blue boxes.

In *Agrobacterium*-mediated plant transformation methods, a cleavage within the 25-bp right border (RB) sequence by a virD1/D2 protein complex is needed for initiation of T-DNA transfer. Also, RB flanking sequences including an ACR and a DR decamer influence the efficacy of T-DNA transfer initiation. The second cleavage for the transferring T-DNA also requires the presence of a 25-bp LB sequence, an AT-rich motif with a consensus sequence positioned at UL as well as LB downstream sequences including a series of C-clusters. Search in publicly available sugar beet genome sequence led to identification of an RB-like (GenBank Accession FR852871.1) and an LB-like (GenBank Accession FR852867.1) sequence with maximum identity to the known T-DNA borders and relevant elements including DR and UL. To design an optimal P-DNA in the inventive binary vectors, a 208-bp sequence of RB-like was fused with a 155-bp of LB-like sequence. Some single nucleotide substitutions for optimization of the essential elements roles by considering the consensus sequences or for making some enzymatic restriction sites for following cloning steps were included. ACR region and C-clusters of *Agrobacterium* pTiC58 vector were placed just before RB and after LB sequences, respectively.

As used throughout this application, unless otherwise indicated Sequence ID 1 ("SEQ ID NO: 1") refers to the sequence of the P-DNA shown in FIG. 1. Specifically, in this application SEQ ID NO: 1 means

```
GTCGACCCGAGGGGAACCCTGTGGTTGGCATGCACATACAAATGGAC
GAACGGATAAACCTTTTCACGCCCTTTTAAATATCCGATTATTCTAA
TAAACGCTCTTTTCTCTTAGGTTTACTATGGAATATATCCTGGGTGT
GGCCGAAGTCTGTTCGGGAAGCTTTAATTCAATGGGTTTACCCAAAG
AAAGGAAATTCTTCAAACAAATTTGAGCTCTGCATCTTTTCAAGGT
ACCATTATATGGTCAGTGTGCTCGAGAGAGAGAAATGAATCTAGAAT
```

-continued

```
TTTCAAGCGGCCGCAACAAATATCGATTCGCCTCTGGAAAAGGGAGG
ACGTGCTATATTGATTTTTGATTCACTCTCAAGCTTGCCCTTATATT
ACATGTCGATATATCCTGCCCAAGCTTCCAGCCAGCCAACAGCTCCC
CGACCAGATCTGTCGAC.
```

FIG. 2 shows analysis of free energy (Kcalmol$^{-1}$) by WEB-THERMODYN across RB and its 200-bp upstream sequence of P-DNA in comparison with T-DNA. The analysis shows that despite the similarity of P- and T-DNA free energy profile, the values calculated for P-DNA were higher than those of T-DNA (149.39 versus 118.21, respectively). It leads to the lower helical stability of P-DNA RB region, which subsequently may facilitate the first cleavage of P-DNA and initiation of P-DNA transfer.

EXAMPLE 1

Construction of pAPn and pAPF2rn Vectors

Figure 3:
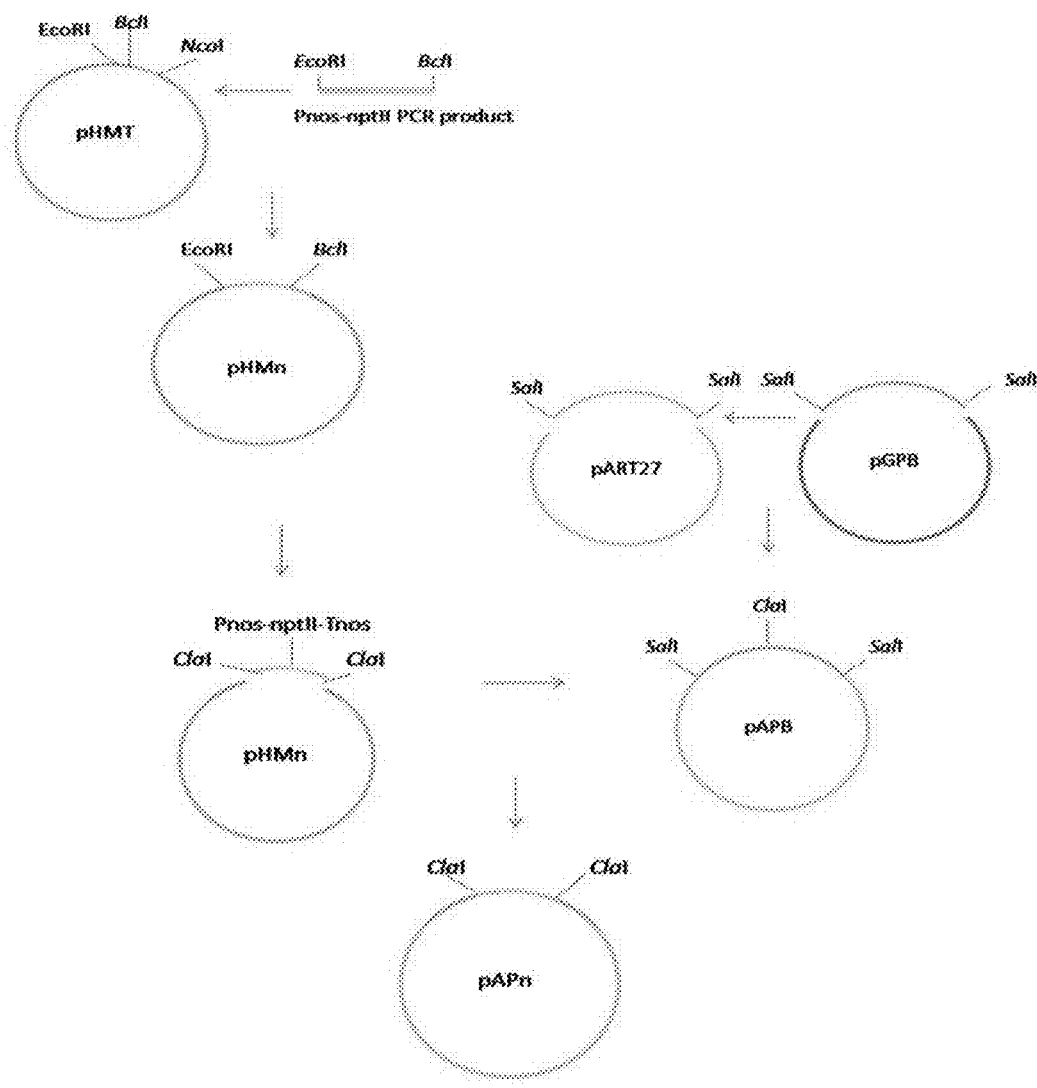
FIG. 3 illustrates the cloning strategy for producing pAPB and subsequently pAPn vectors
Figure 4:
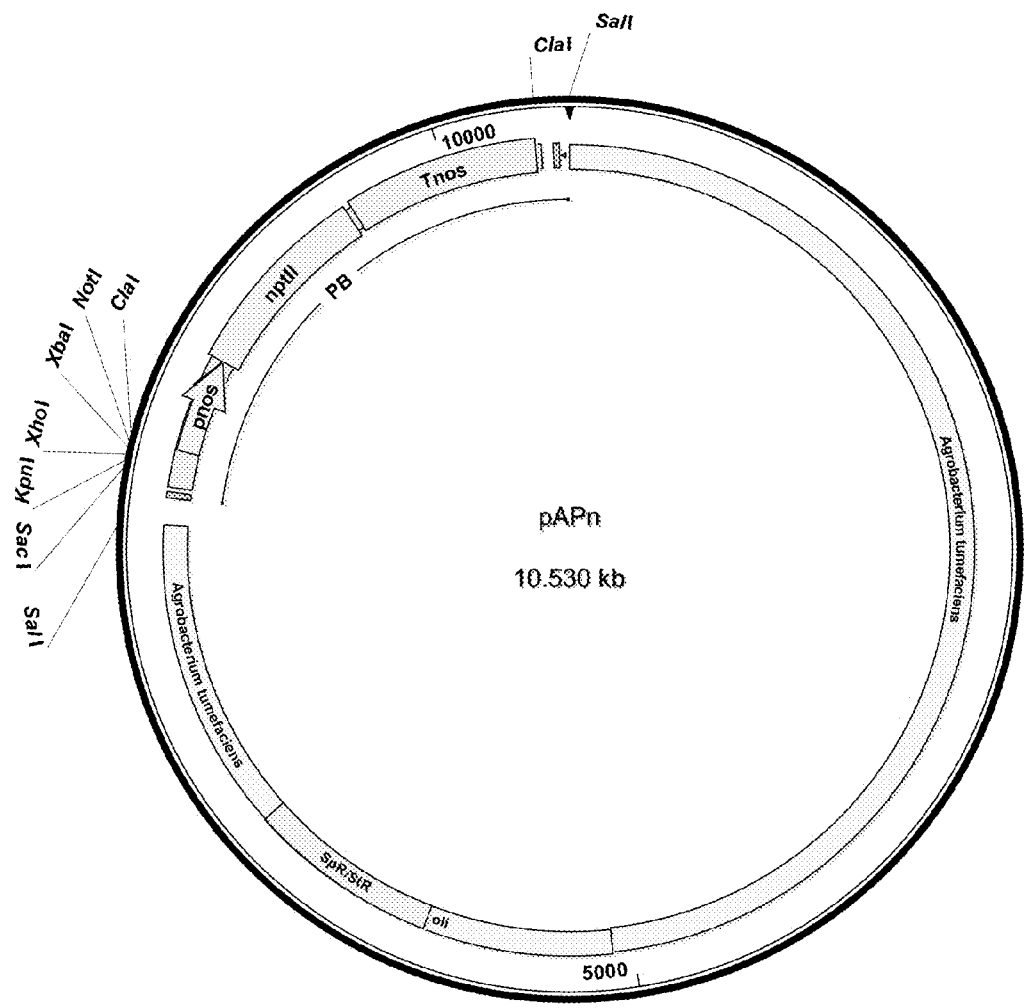
FIG. 4 illustrates the map of pAPn binary vector
Figure 5:
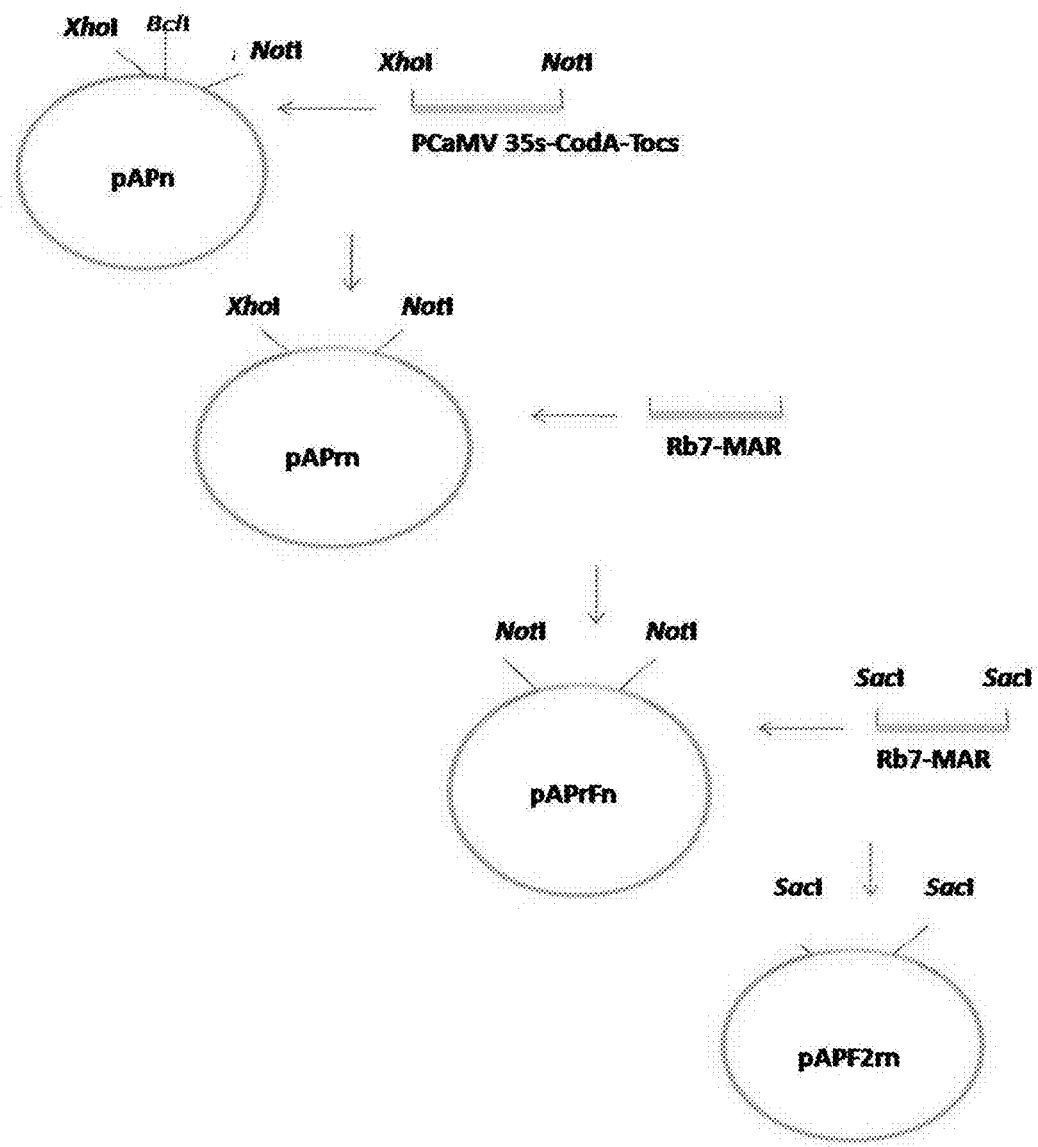
FIG. 5 illustrates the cloning strategy for producing pAPF2rn vector
Figure 6:
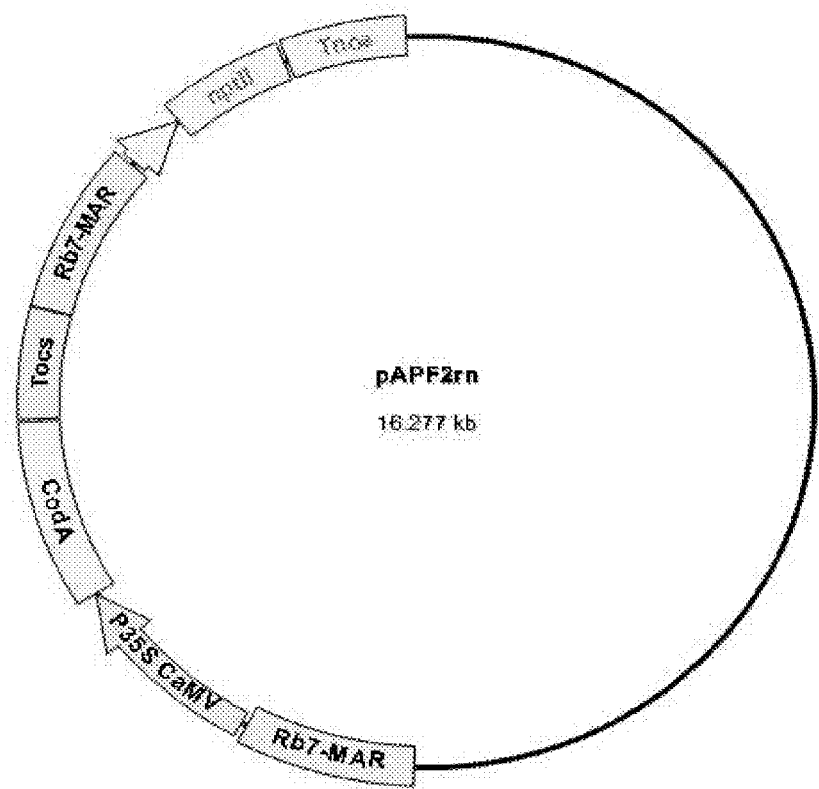
FIG. 6 illustrates the map of pAPF2rn vector

FIG. 1 illustrates the cloning strategy for producing pAPB followed by cloning strategy for producing pAPn constructs. A 283-bp and a 155-bp sequences corresponding to RB and LB of P-DNA, respectively, were selected from sugar beet genome deliberately such that only the essential elements for DNA transfer were included. Moreover, it contains a high A/T content (59.4% versus 51.1% for T-DNA), which may affect initiation of the P-DNA transfer, as well. As illustrated in FIG. 3, pAPB vector was constructed in several steps through conducting conventional digestion and ligation reactions. In fact, the synthesized P-DNA substituted a conventional T-DNA between SalI restriction sites of pART27 binary vector, which is a derivative of pTiC58 carrying elements such as RB, LB, ACR and C-clusters. To examine P-DNA functionality, an expression cassette carrying Pnos-nptII-Tnos encoding neomycin phosphotransferase (nptII) was also cloned between the borders of P-DNA in the ClaI restriction site of pAPB to produce pAPn vector FIG. 4. FIG. 4 illustrates a map of pAPn binary vector. Restriction sites and an example of gene expression cassette for nptII gene are shown. The synthesized PB sequence substituted a conventional T-DNA between SalI restriction sites of pART27 binary vector, which is a derivative of pTiC58 carrying elements such as RB, LB, ACR and C-clusters. Furthermore, two copies of Rb7 matrix attachment regions (MAR) were placed after RB and before LB leading to construct pAPF2rn vector as shown in FIGS. 5 and 6. Specifically, FIG. 5 illustrates a cloning strategy for producing pAPF2rn vector starting from pAPn construct. FIG. 6 illustrates a map of pAPF2rn binary vector. Restriction sites are as shown in FIGS. 4 and 5. An example of gene expression cassette for codA gene is shown in FIG. 6

EXAMPLE 2

Increasing Transformation Rate of Tobacco Cells Using pAPn Vector

Leaf explants of *Nicotiana tabacum* L. cv Xanthi were transformed with *Agrobacterium tumefaciens* strain GV3101 carrying pAPn, the newly developed binary vector containing either P-DNA or pART27, as a conventional binary vector containing T-DNA. Overnight-grown bacterial cultures were precipitated for 10 min at 2800 ×g and re-suspended in 50 ml LB medium containing 100 μM acetosyringone to 0.5 OD600. These cultures were used to infect leaf and petiole segments of tobacco for 10 min. The infected segments were incubated for 72 h on co-culture medium (MS medium supplemented with 400 mg lit-1 cefotaxime, 50 mg lit-1 kanamycin and 0.1% agarose plus 1 mg lit-1 BA and 0.1mg lit-1 IBA) at 25° C. in dark. They subsequently transferred to regeneration medium (MS medium supplemented with 1 mg lit-1 BA, 0.1 mg lit-1 IBA, 300 mg lit-1 cefotaxime, 100 mg lit-1 kanamycin and 0.1% agarose). They were sub-cultured in two week intervals. After two months regenerated shoots were isolated and placed on hormone free growth medium (MS medium supplemented with 300 mg lit-1 cefotaxime, 100 mg lit-1 kanamycin and 0.1% agarose). Transformed plants were monitored by performing a PCR using Pnos-F (5'- GAAT-TCGGCCGGGAGCATGCGAC-3', SEQ ID NO: 2) and nptII-R (5'- TGATCATTTCGAACCCC AGAGTC-3', SEQ ID NO: 3) primer pairs.

As shown in Table 1, the transformation efficiency of pAPn was significantly greater than that of pART27 at $P<0.05$. These results indicate that the transformation efficiency using pAPn vector was 2.3 fold higher than when pART27 vector was used.

TABLE 1

The rates of produced transgenic tobacco shoots using either pAPn or pART27 binary vectors

| Constructs Name | Transfer DNA type | Explant No. | Kanamycin resistant regenerated plants | Regeneration rate[1] | No. of Examined plants with PCR | PCR+ plants | PCR+ Plants rate[2] | Transformation rates[3] |
|---|---|---|---|---|---|---|---|---|
| pART27 | T-DNA | 136 | 45 | 33% | 45 | 35 | 77.8% | 26% |
| pAPn | P-DNA | 302 | 234 | 77% | 74 | 59 | 79.7% | 61% |

[1] The regeneration rate is the frequency of independent kanamycin-resistant regenerated buds per total number of explants multiplied by 100.
[2] The PCR positive rate is the number of PCR positive regenerated plants per total number of examined plants multiplied by 100.
[3] Transformation rate is PCR positive percentage multiplied by regeneration rate.

EXAMPLE 3

Producing Sugar Beet Hairy Root Using pAPn Vector

For hairy root transformation, leaves and petioles of sugar beet variety SBSI-02 were exposed to *Agrobacterium rhizogenes* strain 15834 carrying either pAPn or pART 27 vectors. Overnight-grown bacterial cultures were precipitated for 10 min at 2800×g before re-suspension in 50 ml LB medium containing 100 μM acetosyringone to $OD_{600}$ of 0.5. The infected leaf and petiole segments of sugar beet were incubated for 48 h on co-culture medium (MS supplemented with 100 μM acetosyringon) at 25° C. in dark. They were subsequently transferred to rooting medium (MS supplemented with 400 mg lit$^{-1}$ cefotaxime, 50 mg lit$^{-1}$ kanamycin and 0.1% agarose) and subcultured every two weeks. After 1 month roots were separated and grown in liquid medium (MS supplemented with 400 mg lit$^{-1}$ cefotaxime and 50 mg lit$^{-1}$ kanamycin) while shaking at 100 rpm for two months. Formations of hairy roots were traced by performing a PCR using Pnos-F and nptII-R primer pairs as above.

TABLE 2

Increased rate of hairy root formations using pAPn vector versus pART27 vector

| Constructs Name | Transfer DNA type | Explant No. | Kanamycin resistant roots | Rooting rate[1] | Examined root No. with PCR | PCR+ roots | PCR+ roots percentage[2] | Transformation rates[3] |
|---|---|---|---|---|---|---|---|---|
| pART27 | T-DNA | 36 | 105 | 292% | 25 | 20 | 80 | 234% |
| pAPn | P-DNA | 39 | 205 | 525% | 22 | 22 | 100 | 525% |

[1]The rooting rate is the frequency of independent kanamycin-resistant regenerated hairy roots per total number of explants multiplied by 100.
[2]The PCR positive percentage is the number of PCR positive hairy roots per number of examined plants multiplied by 100.
[3]Transformation rate is PCR positive percentage multiplied by rooting rate.

As shown in Table 2, the frequency of explants producing kanamycin-resistant hairy roots was an average number of 5.2 hairy roots per inoculated explants for pAPn and an average number of 2.9 for pART27. Transformation rate was defined as the PCR-positive percentage of hairy roots per leaf explants. The transformation rate of pAPn was 525% which was significantly ($P<0.05$) higher than that of paRT27 at 234%. As a result, the transformation efficiency of pAPn was 2.2 fold greater than that of pART27 in sugar beet hairy root system. In other words, the engineered sugar beet derived P-DNA used in pAPn binary vector supports more effective transfer of transgene into plant cells than the conventional T-DNA.

TABLE 3

Increased rate of hairy root formations using pAPn or pAPFrn versus pART27 vectors.

| Constructs Name | Transfer DNA type | Explant No. | Kanamycin resistant roots | Rooting rate[1] | Examined root No. with PCR | PCR+ roots | PCR+ roots percentage[2] | Transformation rates[3] |
|---|---|---|---|---|---|---|---|---|
| pART27 | T-DNA | 36 | 105 | 292% | 25 | 20 | 80 | 234% |
| pAPn | P-DNA | 149 | 726 | 487% | 37 | 32 | 86 | 419% |
| pAPF2rn | P-DNA | 106 | 984 | 928% | 53 | 51 | 96 | 891% |

[1]The rooting rate is the frequency of independent kanamycin-resistant regenerated hairy roots per total number of explants multiplied by 100.
[2]The PCR positive percentage is the number of PCR positive hairy roots per number of examined plants multiplied by 100.
[3]Transformation rate is PCR positive percentage multiplied by rooting rate.

EXAMPLE 4

Increasing Transformation Rate of Hairy Roots Using pAPF2rn Vector

To examine effects of MARs on transformation efficiency, two copies of Rb7-MAR were placed in downstream and upstream of pCaMV35S-CodA-Tocs expression cassette using NotI and SacI restriction sites. This expression cassette was produced by cloning of CodA-Tocs in XhoI, NotIalongside of CaMV35S promoter in SacI-XhoI restriction sites of pAPn (FIGS. 5 and 6).

Sugar beet hairy roots transformations via *Agrobacterium rhizogenes* 15834 containing either pAPF2m, pAPn or pART27 were done based on a procedure described EXAMPLE 3. As shown in Table 3, the transformation efficiency of pAPF2rn was 891% and significantly ($P<0.05$) greater than those of pAPn and pART27 rates for 1.7 and 3.8 fold, respectively.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

What is claimed is:

1. A binary vector comprising two plant-derived transfer DNA ("P-DNA"), wherein the binary vector comprises:
   SEQ ID NO: 1;
   a set of ordered unique restriction endonuclease cleavage sites for insertion of the heterologous DNA; and
   matrix attachment region sequences between the LB and RB sequences configured to improve transformation rate and gene expression level in plant.

2. The binary vector of claim 1, wherein the SEQ ID NO: 1 comprises TCTGTTCGGG SEQ ID NO: 4, an optimized engineered DR element.

3. The binary vector of claim 1, wherein the SEQ ID NO: 1 comprises ATTGATTTTTGATTC SEQ ID NO: 5, an optimized engineered UL element.

4. The binary vector of claim 1, wherein the LB and RB sequences are selected from sugar beet genome and optimized for higher transformation rate.

5. A binary vector comprising a sequence of a plant-derived transfer DNA ("P-DNA") comprising SEQ ID NO: 1, wherein:
   the vector further comprises matrix attachment region sequences between the LB and RB sequences that improve transformation rate and gene expression in plant.

6. A method for transforming a plant cell, comprising:
   providing a vector comprising: SEQ ID NO: 1, a set of ordered unique restriction endonuclease cleavage sites for insertion of heterologous DNA, and a heterologous DNA encoding a gene product inserted into the unique restriction site; and
   introducing said vector into the plant cell.

7. The method of claim 6, wherein the RB has a 208 base pair sequence and the LB has a 155 base pair sequence.

8. The method of claim 6, further comprising regenerating a transgenic plant from the transformed plant cell.

9. The method of claim 6, further comprising expression of the heterologous DNA in the plant cell to produce gene product encoded by the heterologous DNA in the plant cell.

10. The method of claim 6, wherein the vector further comprises a selection marker for introduction of the heterologous DNA into the plant cell, the selection market located between the LB and RB sequences.

* * * * *

SEQUENCE LISTING

```
<160> NUMBER OF SEQ ID NOS: 5

<210> SEQ ID NO 1
<211> LENGTH: 440
<212> TYPE: DNA
<213> ORGANISM: Artificial Sequence
<220> FEATURE:
<223> OTHER INFORMATION: Synthetic P-DNA

<400> SEQUENCE: 1
gtcgacccga ggggaaccct gtggttggca tgcacataca aatggacgaa cggataaacc      60
ttttcacgcc cttttaaata tccgattatt ctaataaacg ctcttttctc ttaggtttac     120
tatggaatat atcctgggtg tggccgaagt ctgttcggga agctttaatt caatgggttt     180
acccaaagaa aggaaaattc ttcaaacaaa tttgagctct gcatcttttc aaggtaccat     240
tatatggtca gtgtgctcga gagagagaaa tgaatctaga attttcaagc ggccgcaaca     300
aatatcgatt cgcctctgga aaagggagga cgtgctatat tgattttga ttcactctca      360 agcttgccct tatattacat gtcgatatat cctgcccaag cttccagcca gccaacagct     420
ccccgaccag atctgtcgac                                                 440

<210> SEQ ID NO 2
<211> LENGTH: 23
<212> TYPE: DNA
<213> ORGANISM: Artificial Sequence
<220> FEATURE:
<223> OTHER INFORMATION: Synthetic primer

<400> SEQUENCE: 2
gaattcggcc gggagcatgc gac                                              23

<210> SEQ ID NO 3
<211> LENGTH: 23
<212> TYPE: DNA
<213> ORGANISM: Artificial Sequence
<220> FEATURE:
<223> OTHER INFORMATION: Synthetic primer

<400> SEQUENCE: 3
tgatcatttc gaaccccaga gtc                                              23

<210> SEQ ID NO 4
<211> LENGTH: 10
<212> TYPE: DNA
<213> ORGANISM: Artificial Sequence
<220> FEATURE:
<223> OTHER INFORMATION: Synthetic DR element
```

```
<400> SEQUENCE: 4
tctgttcggg                                                                  10

<210> SEQ ID NO 5
<211> LENGTH: 14
<212> TYPE: DNA
<213> ORGANISM: Artificial Sequence
<220> FEATURE:
<223> OTHER INFORMATION: Synthetic UL element

<400> SEQUENCE: 5
attatttttg attc                                                             14
```